United States Patent [19]

Ho et al.

[11] Patent Number: 5,578,743
[45] Date of Patent: Nov. 26, 1996

[54] CYCLOPYMERIZATION POLYMERS FROM NON-CONJUGATED DIENES

[75] Inventors: Suzzy C. Ho, Dayton; Margaret M. Wu, Skillman, both of N.J.; Yusheng Xiong, Newtown, Pa.

[73] Assignee: Mobil Oil Corporation, Fairfax, Va.

[21] Appl. No.: 416,426

[22] Filed: Apr. 4, 1995

Related U.S. Application Data

[63] Continuation-in-part of Ser. No. 114,881, Sep. 1, 1993, abandoned.

[51] Int. Cl.$^6$ .................. C07C 2/10; C08F 36/20
[52] U.S. Cl. ................ 585/530; 526/104; 526/106; 526/336; 585/10; 585/17; 585/520
[58] Field of Search .................. 585/10, 17, 520, 585/530, 522, 523; 526/104, 106, 336

[56] References Cited

U.S. PATENT DOCUMENTS

| | | | |
|---|---|---|---|
| 3,357,961 | 12/1967 | Makowski et al. | 525/332.1 |
| 3,435,020 | 3/1969 | Olson | 526/159 |
| 4,827,073 | 5/1989 | Wu | 585/530 |
| 4,969,522 | 11/1990 | Whitehurst | 166/278 |
| 5,208,304 | 5/1993 | Waymouth | 526/164 |

*Primary Examiner*—Ponnathapura Achutamurthy
*Attorney, Agent, or Firm*—Ronald A. Bleeker; Malcolm D. Keen

[57] ABSTRACT

Novel homopolymer and copolymer compositions produced from the polymerization of non-conjugated dienes have been discovered. The novel compositions are produced by an equally novel process comprising cyclopolymerization of non-conjugated dienes employing reduced valence state Group VIB metal oxide catalyst on porous support. The preferred catalyst comprises carbon monoxide reduced chromium on silica. Copolymers are formed by copolymerization of non-conjugated dienes with 1-alkenes in contact with the activated chromium on silica catalyst. The compositions are useful as lubricants and additives.

11 Claims, No Drawings

CYCLOPYMERIZATION POLYMERS FROM NON-CONJUGATED DIENES

RELATED APPLICATIONS

This application is a continuation-in-part of pending application Ser. No. 08/114,881 (Docket 7147) filed Sep. 1, 1993.

The invention relates to novel polymer and copolymer compositions produced from the polymerization of non-conjugated symmetrical or unsymmetrical dienes and to the novel process for their production. The invention specifically relates to the cyclopolymerization of non-conjugated dienes employing reduced chromium on silica as catalyst and to copolymers formed with 1-alkenes. The compositions are useful, inter alia, as lubricants and additives.

BACKGROUND OF THE INVENTION

The polymerization of non-conjugated dienes to form polymers and copolymers that incorporate recurring units of cyclic moieties in the polymer or copolymer backbone is known. While it had been presumed that polymerization of non-conjugated dienes produces only cross-linked polymers, cyclopolymerization of diallyl quarternium salts to linear polymers was first reported by G. B. Butler in 1947 (J. Amer. Chem. Soc., 71, 3120). Since then, a large variety of non-conjugated dienes have been reported to undergo cyclopolymerization.

For symmetrical, non-conjugated dienes, it has been shown that all of the well-known methods of polymerization can be employed to initiate cyclopolymerization. Polymerization by free radical initiation, cationic and anionic initiation have been demonstrated. Cyclopolymerization of divinyl benzene has been accomplished using Ziegler-Natta catalysis.

Copolymerization of non-conjugated dienes with vinyl monomers is also known (G. B. Butler, et al., J. Poly. Sci. 48, 279 (1960). Depending upon the comonomer pair and the copolymerization conditions, the product copolymer may contain recurring units of ring moieties plus vinyl moiety or the vinyl and diene moiety may combine to form a common recurring ring moiety.

Additional examples of cyclopolymerization are abundant in the chemical literature. The technology is summarized in the Encyclopedia of Polymer Science and Engineering, Vol. 4, 1986, pp 543–598.

Recently, a novel catalyst system has been reported which has been found to be particularly effective for the polymerization and copolymerization of 1-alkenes. In U. S. Pat. Nos. 4,827,064 and 4,827,073 to M. Wu, incorporated herein by reference, the unique catalyst system is reported. The catalyst is used for the preparation of superior hydrocarbon lubricants having low methyl to methylene branch ratio by oligomerization of alpha olefins. The catalyst comprises reduced valence state Group VIB metal oxide catalyst on porous support. The specific method for lubricant preparation employs as catalyst an activated chromium catalyst comprising carbon monoxide reduced chromium on a silica support. The novel lubricant compositions which can be produced by activated chromium on silica catalysis comprise polyalpha-olefins polymers and/or copolymers.

Although the versatility and effectiveness of activated chromium on silica catalysis for 1-alkene polymerization and benzene alkylation has been well documented, little has been known relative to the reactivity of the catalyst with polyenes, particularly non-conjugated dienes. Despite the abundance of research conducted on cyclopolymerization, activated chromium on silica catalyst has not been reported in the prior art as a catalyst for aliphatic non-conjugated diene cyclopolymerization. Indeed, the uniqueness of the activated chromium catalyst has tended to inhibit those skilled in its use to conclude how it would function in diene polymerization compared to known cyclopolymerization catalysts. Accordingly, the fact, as presented herein, of the activity of reduced chromium on silica catalyst in non-conjugated diene polymerization represents a distinctly unanticipated discovery.

It is an objective of the present invention to provide novel polymer and copolymer compositions comprising atactic polymeric aliphatic hydrocarbon compositions comprising randomly recurring 1-methylene 3-cycloalkyl units.

It is a further object of the present invention to provide a method for the production of the foregoing compositions employing as catalyst reduced chromium on silica for non-conjugated diene polymerization.

Another objective of the present invention is to provide the foregoing compositions in a manner and form compatible with their use as lubricants or lubricant additives.

SUMMARY OF THE INVENTION

Novel polymer and copolymer compositions produced from the polymerization of non-conjugated dienes have been discovered. The novel compositions are produced by an equally novel process comprising cyclopolymerization of non-conjugated dienes employing reduced valence state Group VIB metal oxide catalyst on porous support. The preferred catalyst comprises carbon monoxide reduced chromium on silica. Copolymers are formed by copolymerization of non-conjugated dienes with 1-alkenes in contact with the activated chromium on silica catalyst. The compositions are useful as lubricants and additives.

More particularly, an atactic homopolymer hydrocarbon composition useful as a lubricant has been discovered comprising randomly recurring 1-methylene 3-cycloalkyl units. The composition has a bromine number of between 1.5 and 10 and at least one terminal vinylidene olefin group. The homopolymer comprises irregular head-to-tail enchainment of randomly recurring units in the homopolymer backbone. The homopolymer backbone is without stereochemical regularity. The recurring units have the structure

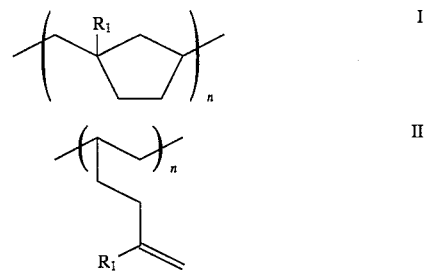

wherein $R_1$ is $C_1$–$C_{20}$ alkyl or hydrogen and n is an integer of 1 to 100. The homopolymer has a molecular weight between 1000 and 10,000.

The process for the production of the polymeric hydrocarbon composition comprises contacting at least one non-conjugated diene having the structure

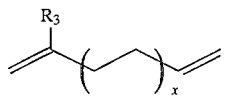

wherein $R_3$ comprises alkyl or hydrogen and x is 1–3, with a reduced valence state Group VIB metal catalyst on a porous support under polymerization conditions whereby the polymeric hydrocarbon composition is produced having a molecular weight of at least 1000. The preferred catalyst comprises $CrO_3$ supported on silica having a pore size of at least 40 Angstroms and reduced by CO or $H_2$ containing gas or metal alkyl reducing agent.

A preferred atactic hydrocarbon homopolymer comprises irregular head-to-tail enchainment of randomly recurring units in the homopolymer backbone without stereochemical regularity with the units having the structures:

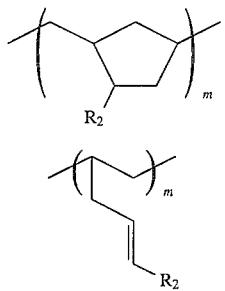

wherein $R_2$ is $C_1$–$C_{20}$ alkyl or hydrogen and m is an integer of 1 to 100. The homopolymer has a bromine number between 1.5 and 10 and molecular weight between 1000 and 10,000.

Hydrocarbon lubricants are produced by a process comprising copolymerizing a mixture comprising between 1 and 99 weight percent of a non-conjugated diene having the foregoing depicted structure, and between 1 and 99 weight percent of at least one $C_3$–$C_{10}$ 1-alkene in contact with a reduced valence state Group VIB metal catalyst on a porous support under copolymerization conditions; and separating a $C_{30}+$ lubricant fraction.

DETAILED DESCRIPTION OF THE INVENTION

The cyclopolymerization reactions of the instant invention are catalyzed by supported metal oxide catalysts, such as Cr compounds on silica or other supported IUPAC Periodic Table Group VIB compounds as described in U.S. Pat. No. 4,827,064 to M. Wu. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The support material usually has high surface area and large pore volumes with average pore size of 40 to about 350 angstroms. The high surface area are beneficial for supporting large amount of highly dispersive, active chromium metal centers and to give maximum efficiency of metal usage, resulting in very high activity catalyst. The support should have large average pore openings of at least 40 angstroms, with an average pore opening of >60 to 300 angstroms preferred. For this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, $RLi$, $R_2Zn$, where R is alkyl, alkoxy, aryl and the like. Preferred are CO or $H_2$ or metal alkyl containing compounds.

Alternatively, the Group VIB metal may be applied to the substrate in reduced form, such as Cr(II) compounds. The catalyst can be used in a batch type reactor or in a fixed bed, continuous-flow reactor.

In general, the support material may be added to a solution of the metal compounds, e.g., acetates or nitrates, etc., and the mixture is then mixed and dried at room temperature. The dry solid gel is purged at successively higher temperatures to about 600° C. for a period of about 16 to 20 hours. Thereafter the catalyst is cooled down under an inert atmosphere to a temperature of about 250 to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence Cr(II) state. Finally, the catalyst is cooled down to room temperature and is ready for use.

The catalyst employed in the instant invention, while selected from Group VIB metal, is different than and distinct over Ziegler-Natta catalyst which is described in "Macromolecules: An Introduction to Polymer Science" by F.A. Bovey and F. H. Winslow, Academic Press, 1979, page 111. Z–N catalyst is a combination of two metals from Groups I–III and Groups IV–VIII. Z–N catalyst produces stereoregular polymers. The catalyst employed in the present invention contains a single metal and produces polymers of random stereoregularity from non-conjugated dienes, particularly polymers with no regularity in head-to-tail enchainment.

The non-conjugated dienes useful in the present invention include those $C_6+$ non-conjugated aliphatic hydrocarbon dienes wherein at least one of the olefinic bonds is an alpha olefin. The second olefinic bond may be an internal olefin or an omega, i.e., terminal olefinic bond. The terminal olefinic bond may be substituted on the penultimate carbon atom with an alkyl group, thereby forming a vinylidene terminal group. Suitable alkyl substituent groups on the penultimate carbon atom include $C_1$–$C_{12}$ alkyl groups with methyl ethyl, propyl and butyl preferred. Methyl is the most preferred. The non-conjugated dienes particularly useful in the present invention have the structure

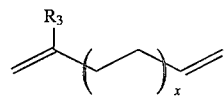

wherein $R_3$ comprises alkyl or hydrogen.

Non-conjugated dienes useful in the present invention include 1,4-hexadiene, 1,5-hexadiene, 2-methyl-1,5-hexadiene, 1,7-octadiene and 1,9-decadiene. Non-conjugated dienes, such as 1,5-hexadiene, 1,4-hexadiene and substituted 2-methyl-1,5-hexadiene or the longer alkadienes can be polymerized by a reduced chromium on silica catalyst to yield novel polymers with unique structures and properties. The polymerization of the non-conjugated dienes proceeds via cyclopolymerization of the dienes.

The polymer formed is atactic with the cycloalkyl moiety randomly distributed throughout the polymer backbone. There is no consistent pattern of head-to-tail cyclopolymerization. Depending on the degree of polymerization, the products can be recovered as liquids or solids.

It has also been discovered that non-conjugated dienes can be copolymerized with 1-alkenes, i.e., alpha olefins, in contact with reduced chromium on silica catalyst to produce copolymers containing randomly recurring cycloalkyl groups and 1-alkene moieties. $C_3$–$C_{12}$ are useful comonomers for copolymerization with $C_6$+ non-conjugated aliphatic hydrocarbon dienes to produce the cyclopolymerization copolymers of the invention. The preferred alpha olefins include propylene and 1-butene. 1-decene is the most preferred.

The cyclopolymerization and copolymerization process of the invention can be carried out at temperatures between 0° C. and 300° C. The preferred temperature for homopolymerization of non-conjugated dienes is between 25° C. and 200° C. while the preferred temperature for copolymerization with 1-alkenes is between 25° C. and 200° C.

The cyclopolymerization of diene by itself or copolymerization with alpha-olefin over activated chromium on silica catalyst is very unexpected. The reaction is not previously reported and the products with unique chemical structures have unusual properties for application as lubricants, additives or chemical intermediates.

The following Examples are provided to illustrate the instant invention. The active chromium on silica catalyst used in the following Examples of cyclopolymerization was prepared as generally described herein and specifically described in Examples 1 or 4 of U.S. Pat. No. 4,827,064.

EXAMPLE 1

Polymerization of 1,5-hexadiene 50 grams of 1,5-hexadiene in 120 gram hexane solvent and 10 grams of an activated Cr/SiO2 catalyst were mixed and heated to about 60° C. for 16 hours. The product was isolated in 20% yield by filtration to remove the catalyst and distilled to remove the light end. The product was recovered as a clear, semi-solid and had a MW of about 1000 by GPC using polystyrene as calibration standards. The solid has the following $^{13}C$ NMR, the results of which are presented in Table 1.

The NMR spectra is consistent with the cyclopolymerization of 1,5-hexadiene over the catalyst to produce a homopolymer of 1,5-hexadiene having a small amount of unsaturated double bonds at the end of each polymer chain and recurring units of irregular enchainment, i.e., head-to-head, head-to-tail, etc. The polymers of the invention do not exhibit stereochemical regularity nor are they formed by block polymerization. The recurring units of poly(1,5-hexadiene) polymerized according to the process of the invention are depicted as A and B as follows with C representing a simplified polymer structure not intended to adequately represent the random structure of the polymer enchainment nor to imply the formation of block polymers:

TABLE 1

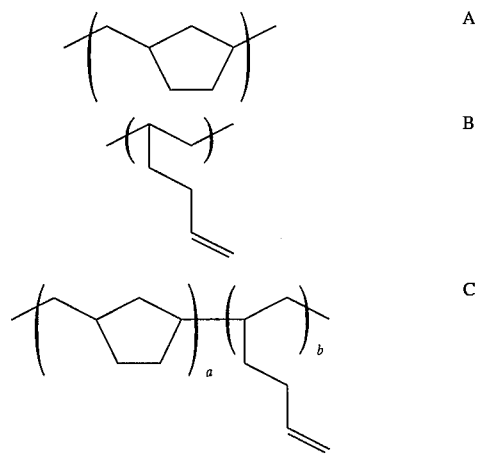

| Chemical shift (in ppm) | Relative intensity | Chemical shift in ppm | Relative intensity |
| --- | --- | --- | --- |
| 24.80 | 146878 | 28.447 | 178717 |
| 29.785 | 224112 | 31.415 | 269853 |
| 31.658 | 171668 | 32.072 | 169424 |
| 32.218 | 173894 | 32.607 | 289969 |
| 32.948 | 683349 | 33.483 | 261031 |
| 33.726 | 376643 | 33.896 | 306500 |
| 36.329 | 153019 | 37.058 | 171026 |
| 37.326 | 602095 | 37.642 | 314152 |
| 37.813 | 257264 | 38.664 | 367105 |
| 38.786 | 397618 | 43.432 | 160422 |
| 43.626 | 202057 | | |

The small amount of unsaturated carbons have $^{13}C$ NMR at 114.12 114.825, 129.882, 140.245 and 144.453 ppm.

Copolymerization of non-conjugated dienes with 1-decene using activated chromium on silica catalyst produces copolymer products with important lubricant properties. Various dienes were copolymerized with 1-decene as depicted in Example 2 and 3 to produce lubricants with unexpectedly high viscosity indices. The results are tabulated in Tables 2 and 3.

Copolymers of dienes and 1-alkenes can be produced from mixtures containing between 1 and 99 weight percent non-conjugated diene and 1–99 weight percent 1-alkene.

EXAMPLE 2

Copolymerization of Dienes with 1-decene 10 grams of various dienes and 90 grams of 1-decene grams were mixed with five grams of activated Cr/SiO2 catalyst and heated to 55° C. for 16 hours. The product was isolated by filtration and distillation to remove light ends. The reaction yields and lube product properties are summarized in Table 2.

TABLE 2

| | Reaction Conditions, Yields and Product Properties | | | |
|---|---|---|---|---|
| Run no. | 2A | 2B | 2C | |
| diene | 1,9-decadiene | 1,7-octadiene | 1,5 hexadiene | none |
| weight of diene | 10 grams | 10 grams | 10 grams | 0 |
| weight of 1-decene | 90 grams | 90 grams | 90 grams | 100 gram |
| lube yield, wt % | 36 | 48 | 69 | >90 |
| lube properties | | | | |
| Visc at 100° C., cS | 638.78 | 1689.39 | 409.1 | ~1000 |
| Visc at 40° C., cS | 7279.22 | 26948.94 | 6120.62 | |
| VI | 283 | 306 | 227 | |
| Bromine No. | 9 | 4 | 5 | <2 |

The lubricant product produced in this manner has high VI and high bromine number, indicating a high degree of unsaturation. Compared to the run without diene, the lube product will have a bromine number of <2. This unsaturation is useful for further functionalization, for example, to couple with maleic anhydride for ashless detergent synthesis.

EXAMPLE 3

Copolymerization of 1-butene with 1,5-Hexadiene 1,5-hexadiene and 1-butene of different proportion were added to an autoclave at 140° C. The reaction conditions, liquid product properties and yields summarized in Table 3. The products produced from copolymerization of diene have higher bromine number than the product without diene addition. This unsaturation is useful for other functionalization reaction.

Example 4 presents the polymerization of 1,4-hexadiene as an illustration of the capability of activated chromium on silica support to cyclopolymerize non-conjugated dienes having internal olefinic bonds.

EXAMPLE 4

1,4-hexadiene Polymerization over Cr/SiO2 Catalyst.

1,4-Hexadiene polymerized over an activated Cr/SiO2 catalyst to give a solid polymer, the results of which are presented in Table 4. The polymer is a cyclopolymerized product and is a solid at room temperature. The product structure was confirmed by $^1$H-NMR and $_{13}$C-NMR. The proton NMR showed that the product polymer contained very little olefinic double bond unsaturation. This is important evidence that the product was a cyclic product with no

TABLE 3

| | Copolymerization of 1-butene with 1,5-Hexadiene | | | | | | |
|---|---|---|---|---|---|---|---|
| Sample No. | 3A | 3B | 3C | 3D | 3E | 3F | 3G |
| Reaction Conditions | | | | | | | |
| Temp, °C. | 140 | 140 | 140 | 140 | 140 | 140 | 140 |
| Feed Rates | | | | | | | |
| 1-C4, g/hr | 120 | 120 | 120 | 120 | 120 | 60 | 60 |
| 1,5 Hexadiene | 0 | 13.8 | 13.8 | 13.8 | 13.8 | 22 | 22 |
| molar ratio of diene/1-butene | 0 | 0.08 | 0.08 | 0.08 | 0.08 | 0.25 | 0.25 |
| conversion to liq. | 94 | 83 | 77 | 67 | 100 | 100 | 100 |
| Liquid composition | | | | | | | |
| C 12– | 11 | | 3 | 5 | | 8 | 7 |
| C 12–20 | 7 | 18 | 6 | 7 | | 8 | 14 |
| C20–30 | 6 | | 6 | 10 | | 10 | 9 |
| C30+ | 76 | 82 | 86 | 78 | | 74 | 71 |
| C30 + Residue properties | | | | | | | |
| V100° C., CS | 69.96 | 72.94 | 59.19 | 67.16 | 44.97 | 40.4 | 33.59 |
| V40° C., | 2191.63 | 2010.95 | 17881.3 | 1949.31 | 1222.12 | 838.03 | 635.77 |
| VI | 81 | 90 | 75 | 84 | 68 | 84 | 81 |
| Bromine no | 11 | 26 | 33 | 29 | 32 | 31 | 40 |
| C30 + residual distillate | 74 | 78 | 67 | 67 | 76 | 63 | 80 |
| % 1,5HD-cyclization | 0 | 87 | 84 | 84 | 81 | 93 | 90 |

Unexpectedly, the process of the invention polymerizes non-conjugated dienes via cyclopolymerization even when the dienes are a combination of alpha olefin and internal olefin.

olefinic double bond remaining in the structure. Based on the proton NMR, it was calculated that at least 80% of the diene produced cyclic product. Furthermore, the spectra indicated that the cyclic product had no structural regularity. The backbone of the polymer was atactic and contained cis and trans cyclic polymer with no head-to-tail regularity. The product has a low molecular weight and a relatively narrow molecular weight distribution which rules out the possibility of a cross linked polymer structure.

The product is very unexpected because internal olefins are usually inert toward the Cr/SiO2 catalyst. However, in present case, the internal double bond participated in the polymerization reaction and, even more surprisingly, the two double bonds cyclized to give an unusual polymer useful as additives for lube or plastic processing.

The polymerization reaction of 1,4-hexadiene was carried out by addition of 2.5 g of catalyst to 10 g of 1,4-hexadiene in a 50 ml-Schlenk flask at 60° C. The reaction mixture was stirred for 2 hour and the polymer became viscous and solidified when cooled to room temperature. Hot tetrahydrofuran was used to dissolve the polymer. The solution was filtered to remove the catalyst. After evaporation of solvent, the product was dried in vacuum to give 6 g of white solid.

The following structures depict the recurring units formed by polymerization of 1,4-hexadiene by the process of the invention where $R_2$ is methyl and m is an integer between 1 and 100.

TABLE 4

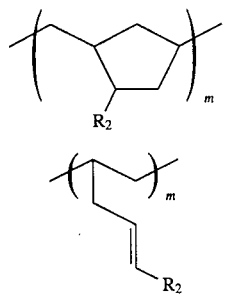

1,4-hexadiene Polymerization over Cr/SiO2 Catalyst

| Run No | 4A | 4B | 4C |
| --- | --- | --- | --- |
| Reaction Temp. °C. | 90 | 60 | 70 |
| Conversion, wt % | 16 | 60 | 58 |
| Product MWn | 2000 | 4000 | 2900 |
| MWw/MWn | 3 | 5 | 3.4 |

Internal olefins that can be employed in the present invention include those having the structure

where y is 1-3 and z is at least 1.

Substituted dienes can also be utilized in the process of the invention to produce polymers by cyclopolymerization. Example 5 depicts this capability by the polymerization of 2-methyl-1,5-hexadiene (MHD) in contact with activated chromium catalyst on silica support. The results are tabulated in Table 5.

EXAMPLE 5

2-methyl-1,5-hexadiene (MHD) Polymerization over Cr/SiO2

MHD polymerized over Cr/SiO2 catalyst to give a liquid product with cyclized structure in the polymer backbone. The product structure was confirmed by $^1$H-NMR and $_{13}$C-NMR spectra. The proton NMR spectrum showed that the product polymer contained very little unsaturation. This is important evidence that the product is a cyclized polymer with little olefinic double bond unsaturation left in the polymer. Based on $_1$H-NMR integration, it was calculated that at least 70% of the second double bond participated in the cyclization reaction. Furthermore, the polycyclic product has no structural regularity. The backbone of the polymer was atactic with no head-to-tail regularity and contained both cis and trans isomers.

The polymerization reaction of 2-methyl-1,5-hexadiene was carried out by addition of 2.0 g of catalyst to 10 g of 2-methyl-1,4-hexadiene in a 50 ml-Schlenk flask at 80° C. The reaction mixture was stirred at 80° C. for 20 hour. The mixture was filtered to remove catalyst. The filtrate was distilled to remove any volatile light fractions to yield 0.75 g of colorless oil. The analytical results are presented in Table 5. The liquid polymer is much more viscous at room temperature than polymers of similar molecular weight from 1-decene. The polymer product can be used as VI improver or lube basestock with novel properties.

TABLE 5

Polymerization of 2-MHD over Cr/SiO2 catalyst

| Run No | 5A | 5B |
| --- | --- | --- |
| Reaction Temp. °C. | 90 | 80 |
| Conversion, wt % | 10 | 7.5 |
| MWn | 1000 | 1100 |
| MWw/MWn | 3 | 3 |

MHD and similarly substituted non-conjugated dienes can also be copolymerized with 1-alkenes over Cr/SiO$_2$ catalyst, analogous to the capability of unsubstituted dienes in the present invention. Example 6 depict this capability with results presented in Table 6.

EXAMPLE 6

Copolymerization of 2-methyl-1,5-hexadiene (MHD) and 1-decene

The copolymerization reactions were carried out by addition of catalyst (10–15% by wt.) to the mixture of 1-decene and the diene. The diene:decene ratio employed were 0:100, 5:95, 10:90, 100:0, as presented in Table 6 along with reaction temperature and results. The product was isolated by filtration and vacuum distillation to remove catalyst and volatile light fractions. The products are colorless oils with analysis shown in Table 6.

TABLE 6

| Run No. | 6A | 6B | 6C | 6D |
| --- | --- | --- | --- | --- |
| Reaction temp. °C. | 75–80 | 75–80 | 75–80 | 90 |
| wt % MHD | 0 | 5 | 10 | 100 |
| wt % 1-decene | 100 | 95 | 90 | 0 |
| Conversion wt % | 93 | 60 | 50 | 10 |
| Product MWn | 4800 | 2700 | 1500 | 1000 |
| Bromine No | 15 | 15 | 20 | — |

The bromine numbers of the runs of Example 6 with diene incorporation show higher bromine number than without any diene addition.

The cyclopolymerization of diene over an activated chromium on silica catalyst produced novel polymers with cyclic structures in the backbone or with a higher degree of unsaturation. These cyclic polymers have unusual properties and can be used in lube or plastic additives. The polymers with higher degrees of unsaturation may also be used as starting material for additive synthesis.

What is claimed is:

1. An atactic liquid hydrocarbon homopolymer comprising irregular head-to-tail enchainment of randomly recurring units in the homopolymer backbone, said units having the structure

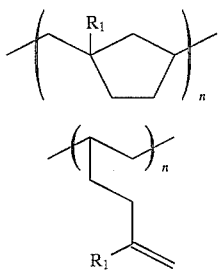

wherein $R_1$ is $C_1$–$C_{20}$ alkyl or hydrogen and n is an integer of 1 to 100, said homopolymer having a bromine number between 1.5 and 10 and molecular weight between 1000 and 10,000.

2. The composition of claim 1 having a molecular weight of at least 1000.

3. The composition of claim 1 wherein $R_1$ is methyl.

4. An atactic liquid hydrocarbon homopolymer comprising irregular head-to-tail enchainment of randomly recurring units in the homopolymer backbone, said units having the structure

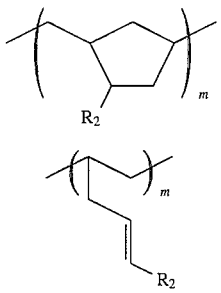

wherein $R_2$ is $C_1$–$C_{20}$ alkyl or hydrogen and m is an integer of 1 to 100, said homopolymer having a bromine number between 1.5 and 10 and molecular weight between 1000 and 10,000.

5. The homopolymer of claim 4 wherein $R_2$ is methyl, said homopolymer comprising the product of a process comprising contacting 1,4-hexadiene with CO reduced $CrO_3$ on silica support under polymerization conditions, said support having a pore size of at least 40 Angstroms.

6. The homopolymer of claim 5 wherein said polymerization conditions comprise temperature between 25° C. and 200° C.

7. A process for the production of an atactic liquid hydrocarbon homopolymer lubricant comprising polymerizing at least one non-conjugated diene having the structure

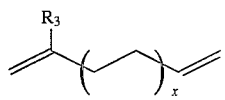

wherein $R_3$ comprises alkyl or hydrogen, and x has a value of 1–3 in contact with a reduced valence state Group VIB metal catalyst on a porous support under polymerization conditions, wherein said homopolymer contains irregular head-to-tail enchainment of randomly recurring units in the homopolymer backbone, said units having the structure

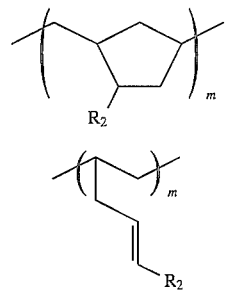

wherein $R_2$ is $C_1$–$C_{20}$ alkyl or hydrogen and m is an integer of 1 to 100, said homopolymer having a bromine number between 1.5 and 10 and a molecular weight of at least 1000.

8. The process of claim 7 wherein said metal catalyst comprises $CrO_3$ on silica support having a pore size of at least 40 Angstroms, said catalyst reduced by carbon monoxide, hydrogen containing gas or metal alkyl reducing agent.

9. The process of claim 7 wherein said polymerization conditions comprise temperature between 25° C. and 200° C.

10. The process of claim 7 wherein said temperature is between 50° C. and 95° C.

11. The process of claim 7 wherein said non-conjugated diene is selected from the group consisting of 1,4-hexadiene, 1,5-hexadiene, 2-methyl-1,5-hexadiene, 1,7-octadiene and 1,9-decadiene.

* * * * *